(12) United States Patent
Bertan et al.

(10) Patent No.: US 6,719,753 B1
(45) Date of Patent: Apr. 13, 2004

(54) MEANS AND METHOD FOR ENERGIZING A FLASH LAMP

(76) Inventors: Howard Stephen Bertan, 41 Moss La., Jericho, NY (US) 11753; Kenneth Lawrence Short, 142 Quaker Path, Setauket, NY (US) 11733

( * ) Notice: Subject to any disclaimer, the term of this patent is extended or adjusted under 35 U.S.C. 154(b) by 115 days.

(21) Appl. No.: 10/177,971

(22) Filed: Jun. 22, 2002

Related U.S. Application Data (62) Division of application No. 09/384,122, filed on Aug. 27, 1999, now Pat. No. 6,461,348.

(51) Int. Cl.[7] .............................................. A61B 18/18
(52) U.S. Cl. ....................... 606/9; 315/200 A; 315/214; 315/241 R; 315/244
(58) Field of Search ................ 606/9–13, 36; 315/214, 241, 241 R, 244, 200 A; 607/88

(56) References Cited

U.S. PATENT DOCUMENTS

| | | | | |
|---|---|---|---|---|
| 3,693,623 A | | 9/1972 | Harte et al. | |
| 3,834,391 A | * | 9/1974 | Block | 606/9 |
| 4,388,924 A | * | 6/1983 | Weissman et al. | 606/9 |
| 4,484,107 A | | 11/1984 | Kaneda | |
| 4,550,275 A | | 10/1985 | O'Loughlin | |
| 4,608,978 A | | 9/1986 | Rohr | |
| 4,617,926 A | * | 10/1986 | Sutton | 606/9 |
| 4,743,809 A | | 5/1988 | Vlahos | |
| 5,026,369 A | * | 6/1991 | Cole | 606/36 |
| 5,105,126 A | * | 4/1992 | Girard, Jr. | 315/241 R |
| 5,226,907 A | * | 7/1993 | Tankovich | 606/9 |
| 5,381,077 A | | 1/1995 | McGuire | |
| 5,425,728 A | * | 6/1995 | Tankovich | 606/9 |
| 5,595,568 A | * | 1/1997 | Anderson et al. | 606/9 |
| 5,735,844 A | * | 4/1998 | Anderson et al. | 606/9 |

* cited by examiner

Primary Examiner—David M. Shay
(74) Attorney, Agent, or Firm—Island Patent; F.S. Tierno (57) ABSTRACT

A method and structure for energizing a flash lamp for producing a high energy light pulse, with the flash lamp energized by a flattened and extended current pulse. The method includes collecting and storing energy for delivery to the flash lamp when triggered. A triggering of the flash lamp resulting in a delivering of the collected and stored energy to the flash lamp in the form of an amplitude controlled (flattened) and duration controlled (extended) current pulse.

13 Claims, 5 Drawing Sheets

MEANS AND METHOD FOR ENERGIZING A FLASH LAMP

CROSS REFERENCE TO RELATED APPLICATION

The subject matter provided herein represents a continuing application of application Ser. No. 09/384,122 filed on Aug. 27, 1999 now U.S. Pat. No. 6,461,348, which is hereby incorporated by reference.

TECHNICAL FIELD

The present invention relates generally to methods of energizing flash lamps. More particularly, the invention relates to a method of energizing a flash lamp with a flattened and extended current pulse, or equivalently, a current pulse having a controlled amplitude and duration.

BACKGROUND ART

Prior art devices employing triggered flash lamps most often employ a direct current (DC) power supply with an output coupled to one or more large energy storage capacitors. The capacitor or parallel capacitors serve as a current reservoir capable of delivering a high amplitude, short duration, current pulse. Such an arrangement usually has the capacitor(s) directly coupled to a power input coupling of the flash lamp. When the flash lamp is triggered, a large amplitude current pulse, as depicted in FIG. 1B, is delivered to the flash lamp, producing a high intensity light pulse. If it is determined that the energy level of the light pulse is inadequate, the output level of the DC power supply, or the total energy storage capacitance, is increased so that a larger amplitude current pulse is available for delivery to energize the flash lamp. When considering size and cost constraints of higher power flash lamps, along with the need for very high energy light pulses in certain applications, often prior art devices operate flash lamps incorporated therein at or above peak/maximum recommended instantaneous operating levels (e.g., as specified by the manufacturer). Accordingly, the life expectancy of a typical flash lamp operated at these excessive current levels is significantly reduced.

Therefore, skilled individuals will appreciate and understand a need for new and improved means and methods for energizing flash lamps that aid in maximizing light energy output from flash lamps, without severely reducing the flash lamp operating lifetime. A full understanding of the present invention, including an understanding of a number of capabilities, characteristics, and associated novel features, will result from a careful review of the description and figures of several preferable embodiments provided herein. Attention is called to the fact, however, that the drawings and descriptions are illustrative only. Variations and alternate embodiments are certainly contemplated as being part of the invention, limited only by the scope of the appended claims.

SUMMARY OF THE INVENTION

In accordance with the invention, means and a method are provided for energizing a triggerable flash lamp. A preferred energizing method taught includes collecting and storing energy for delivery to the flash lamp. The energy that is collected and stored may be provided by a direct current (DC) power supply having an energy providing output. The collected energy is then delivered to the flash lamp in the form of a current pulse having a controlled amplitude over a short duration. Equivalently, the current pulse may be said to be "flattened and extended", when compared to typical current pulses used to energize the flash lamp when triggered. Specifically, the short duration, flattened current pulse is coupled and delivered to an energy input coupling of the flash lamp when the flash lamp is triggered, thereby producing the high energy light pulse.

The step of collecting and storing energy may most preferably be supported by including an energy storage module that is interposed between the output of the power supply module and the energy input coupling of the flash lamp. This arrangement would further preferably provide for the energy storage module to be structured having an output impedance that is matched to an input impedance of the energy input coupling of the flash lamp (when triggered and while delivering the current pulse to the flash lamp).

A preferred embodiment of the energy storage module may be provided by a charged delay line composed of a series-parallel arrangement of inductors and capacitors providing a simulated lumped-element charged delay line. When the output impedance of the charged delay line is matched to the energy input coupling of the flash lamp, the desired amplitude controlled (flattened) and duration controlled (extended) current pulse may be readily delivered to the flash lamp in order to fully energize the flash lamp while limiting the peak current to a level substantially below a maximum operating current that would typically be employed by prior art devices.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

| Partial List Of Reference Numerals | |
|---|---|
| 12, 12a, 12b | power supplying apparatus |
| 15 | flash lamp |
| 16 | flash lamp assembly |
| 16a | energy input coupling (of flash lamp assembly 16) |
| 16b | trigger terminal (of flash lamp assembly 16) |
| 22, 22a | (flattened and extended) current pulse |
| 26 | power source |
| 30 | power supply module |

-continued

Partial List Of Reference Numerals

| | |
|---|---|
| 30a | output of power supply module 30 |
| 32 | energy storage module |
| 32a | output (of the energy storage module 32) |
| 34 | charged delay line |
| 36 | inductor |
| 38 | capacitor |
| 42 | optical coupler |
| 44 | directed optical light energy or light rays |
| 64 | embedded controller (logic module) |
| 64a, 64b | operative links |
| 64c | trigger signal |
| 88 | feedback signal |
| 90 | optical detection means |

DETAILED DESCRIPTION AND MODES OF THE INVENTION

It is important to establish the definition of a number of terms that will be used throughout this disclosure. The term 'high energy light pulse' may be assumed to indicate a light pulse having a sufficient intensity (and or total energy) level for its intended use. For example, preferred intensity levels may include light pulses having an energy of 0.1 joules to 5 joules. Also, the terms 'high energy light pulse' and 'light pulse' may be assumed to be synonymous. The terms 'sufficient duration' and 'correct duration', when applied to the duration of a suitable high energy light pulse produced in accordance with the invention, may be assumed to vary considerably with the application in which the flash lamp and high energy light pulses are utilized. For example, when considering a photo-epilation apparatus, a sufficiently short duration would most preferably be in the micro-second range, and selected to prevent significant epidermal self-cooling, while causing the desired photo-thermal epilation. The term 'flattened and extended current pulse', which describes the general shape of current pulses produced by the apparatus of the invention, may be assumed to describe an amplitude controlled (flattened) and duration controlled (extended) current pulse. As such, a flattened and extended current pulse will be a current pulse having a period or interval during which a substantially constant (flattened) current level is generated. This is in contrast to the common spike current pulse in which the level of current rapidly rises, and then rapidly falls, with a very short period during which the current is constant. Flattened and extended current pulses will be described in significant detail hereinafter. A number of other terms and definitions will be provided in the discussions that follow, as required, for a clear and complete understanding of the present invention.

Figure 1A:
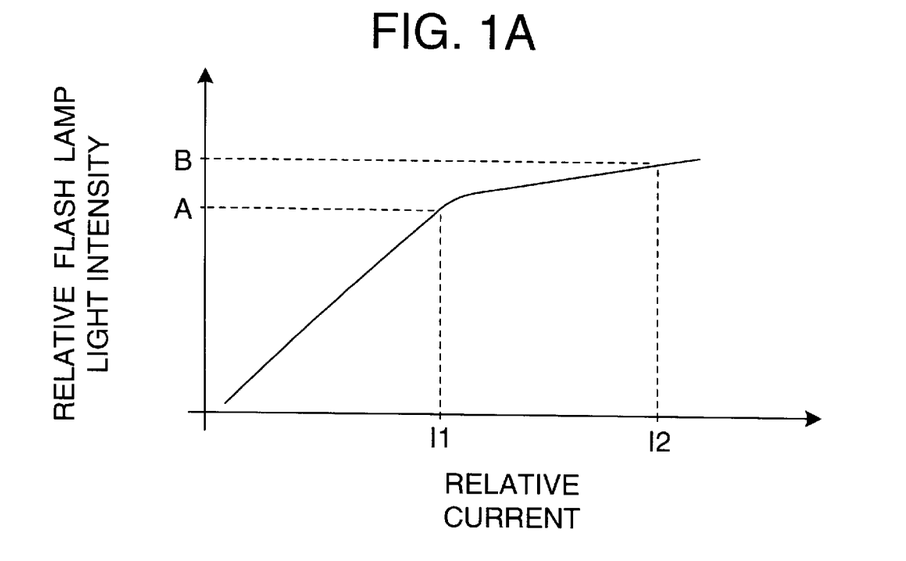
FIG. 1A provides a piecewise linear graph of relative light intensity produced by a gas filled flash lamp with respect to the relative current employed to energize the flash lamp.
Figure 1B:
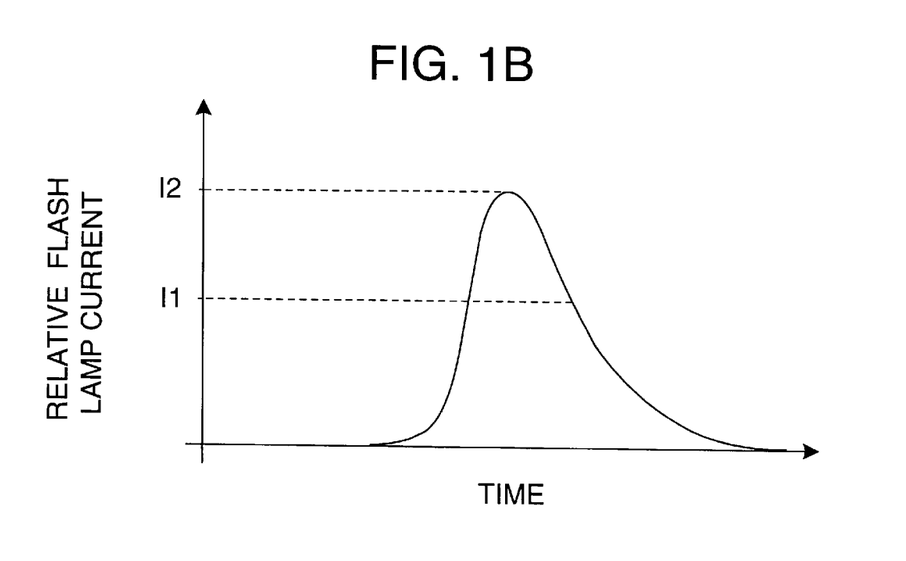
FIG. 1B depicts a current pulse, as a function of time, which is commonly employed to energize a flash lamp when triggered.

Referring now to FIG. 1A, there is illustrated an approximated piece-wise linear relationship of relative current versus relative flash lamp light intensity produced by a flash lamp. As understood by skilled persons, the light produced by a xenon flash lamp is not linear after the current is increased above a first desired operating level. As can be seen in FIG. 1A, a linear relationship exists until the relative current applied to the flash lamp reaches a level I1. A corresponding relative light intensity or output level produced by a current level I1 may be assumed to be light intensity level A. The current level I1 may be termed a 'first desired current limit' Beyond the current level I1, a significant current increase is required to produce a modest increase in the light output. For example, as can be seen in FIG. 1A, an approximate doubling of current from a level of I1 to a level of I2, produces a relatively small increase in the light intensity. In addition, the life expectancy of the flash lamp may be reduced considerably when operated at or near current level I2.

Figure 1C:
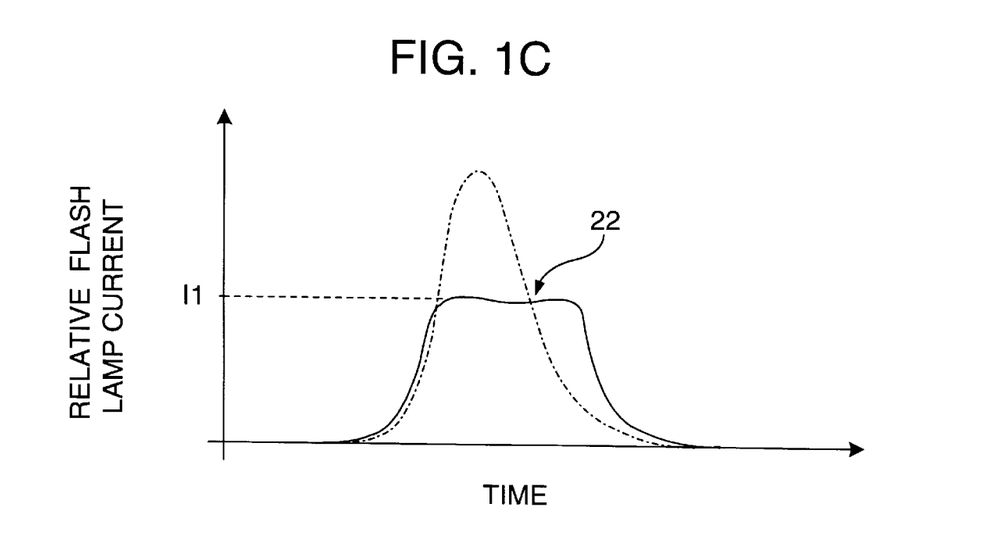
FIGS. 1C and 1D show flattened and preferably extended current pulses of the invention, contrasted with prior art pulses (shown in dotted lines), that may be coupled to energize a flash lamp in order to produce a high energy light pulse in accordance with the invention.
Figure 1D:
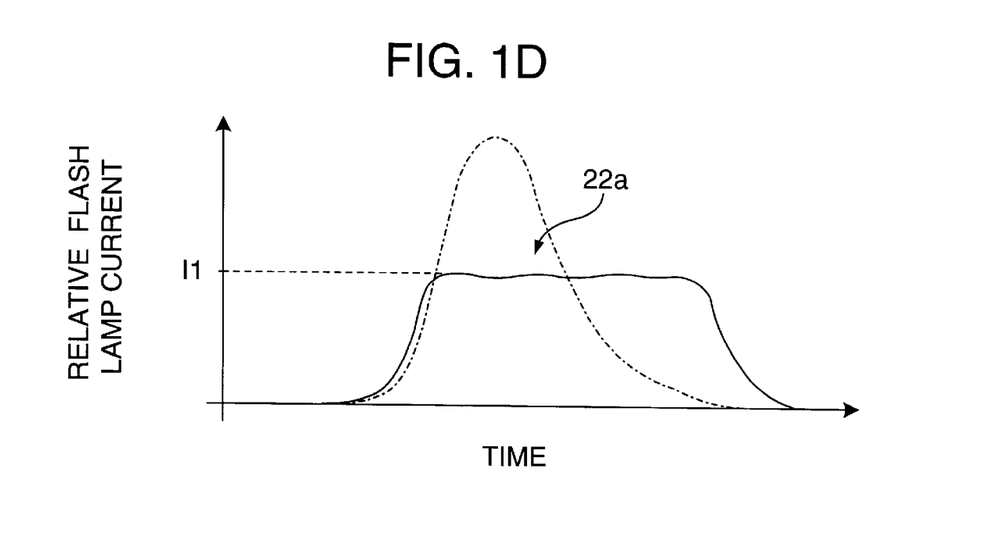

As can be seen in FIG. 1B, a typical current pulse that is produced by coupling the energy stored by a simple capacitor based energy storage arrangement is a simple current spike. As such, if I1 is assumed to be a safe and desired current level, but I2 is the current level that is required to produce the desired light intensity level, such a current pulse does not safely and efficiently energize the flash lamp. It would be most desirable to alter the energy storage arrangement for producing and delivering a current pulse that has a flattened and extended shape. For example, the flattened and extended current pulses 22 and 22a depicted in FIGS. 1C and 1D, respectively, each provide for an efficient energizing of a flash lamp (when coupled to the energy input coupling thereof). The current pulses 22/22a of FIGS. 1C and 1D enable an efficient current level to be established and maintained for a suitable duration or interval. This reduced current level is maintained during the interval in order to produce a light pulse of a desired total energy and of a sufficiently short or otherwise correct/desired duration. Importantly, it has been determined that when a flash lamp is energized by a flattened and extended current pulse, such as current pulses 22/22a, a xenon flash lamp can be operated at a peak energy level that is significantly above the maximum peak energy level recommended by the flash lamp manufacturer—with no apparent reduction in the operating life of the flash lamp as long as the average power rating for the lamp is not exceeded. This unexpected result is essentially due to the reduction of the peak current to a lower and safer level. It may be noted that the expression flattened and extended current pulse, as depicted in FIGS. 1C and 1D, may be considered flattened and extended when compared to the spike-shaped current pulses (that are depicted using dotted lines). Further, as can be seen, the peak current amplitude of the flattened pulse is most preferably established at a level well below the peak of a spike current pulse. A most desired flattened and extended current pulse would also hold its peak (or near peak level) for a longer duration than the spike current pulse width (as is clearly illustrated in FIGS. 1C and 1D).

Figure 2:
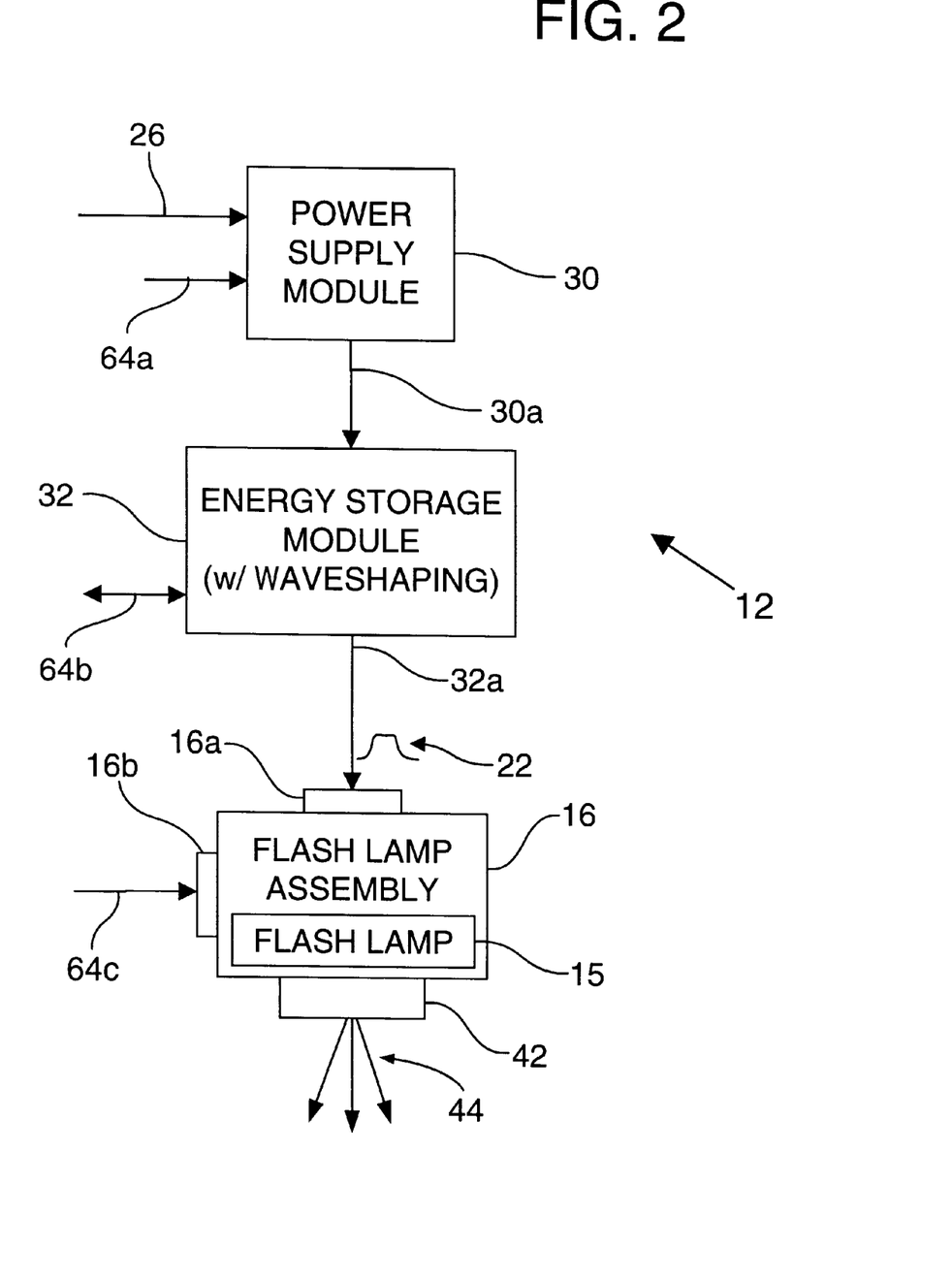
FIG. 2 illustrates a high level block diagram of an embodiment of a preferred structure for an energy supplying means supporting the method of the invention.

Turning now to FIG. 2, there is shown therein a high level conceptual block diagram of a first preferred structure for supporting the method of the invention. A first major functional block is provided by a power supply module 30 having coupled thereto a power source 26. Power supply module 30 is configured with an output 30a for providing energy that is collected and stored during an interval between each produced high energy light pulse. A preferred power supply or power supply module 30 may have an output voltage of 300 to 1000 volts, and an average output current of approximately 5 to 50 milli-amperes. The energy provided by the power supply module 30 is collected and stored in an energy storage module 32. The energy stored in the energy storage module 32 will be delivered from output 32a in the form of a flattened and preferably extended current pulse 22 that is coupled to the energy input coupling 16a for energizing a flash lamp 15 of the flash lamp assembly 16. The current pulse 22 is produced and delivered to the flash lamp 15 when the flash lamp is triggered. For example, when operating in a pulsed mode, triggering is effected by employing a trigger signal coupled to the trigger terminal 16b by operative link 64c. It may be noted that in preferred embodiments of the invention the flattened and extended current pulse 22 may be have a maximum instantaneous current level of approximately 1000 to 5000 amperes. A desired or required current level may be established by the respective application in which the invention is employed. Skilled individuals will further understand that the power supply module 30 may continue to supply energy to the energy storage module 32 during the producing of a light pulse. However, the amount of energy delivered during this short interval, while the light pulse is produced, is quite small and has a negligible effect on the energy delivered by the energy storage module 32 when energizing the flash lamp.

The flash lamp 15 produces a light pulse each time it is triggered, with triggering preferably provided in a periodic fashion with a delay interval provided between each respective triggering. The delay is provided so that sufficient energy may be collected and stored by the energy storage module 32 for properly energizing the flash lamp 15 when next triggered. As each respective light pulse is produced, the light energy may be coupled to an optical collector or coupler 42. The optical coupler 42 may be employed to direct and couple the light energy depicted by light rays 44 of FIG. 2, as needed.

Figure 3:
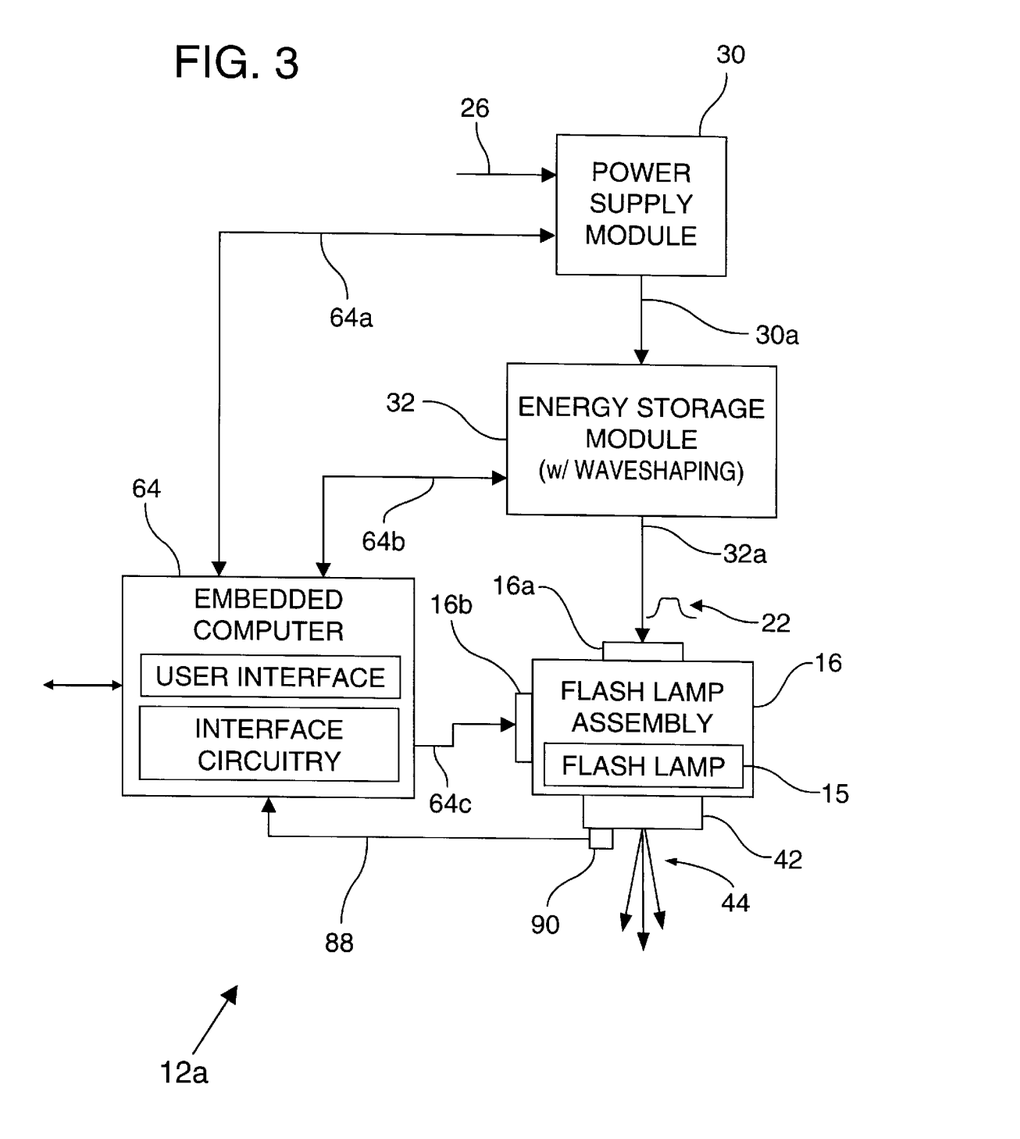
FIG. 3 provides a high level block diagram of another preferred embodiment of an energy supplying means employing aspects of the invention.

Referring now to FIG. 3, there is provided a block diagram of another preferred power supplying apparatus 12a of the invention. As shown, the embodiment depicted includes a power supply module 30, energy storage module 32, and the flash lamp assembly 16, all of which function as indicated above when referring to the embodiment of FIG. 2. The embodiment of FIG. 3 further includes an embedded computer 64 (preferably having a user interface), which may be very generally termed a 'control means'. The embedded computer 64 may be included for several purposes. First, in applications where an automatic, periodic triggering of the flash lamp 15 is required, the embedded computer 64 may be configured to periodically trigger the flash lamp assembly via the operative link 64c coupled to the trigger terminal 16b. This arrangement would provide for the generation of a temporally spaced succession of light pulses, without any direct user or operator involvement.

In addition, the embedded computer 64 may be structured to produce operative link 64a, which may be provided for adjusting parameters of the power supply module 30. For example, operative link 64a may be provided to enable the output voltage produced at output 30a to be increased or decreased so that the energy level of the high energy light pulse may be adjusted to required levels. In a most preferred embodiment of the invention, the power supplying arrangement 12a may provide for an adjusting of the energy level of the high energy light pulse by providing a feedback signal 88. As illustrated in FIG. 3, an optical detection means 90 may be included to sample or detect a precise sample of the energy of a produced light pulse. The term 'precise sample' is to be defined as a known portion or fraction of the light pulse energy produced, which may be employed to enable calibration of the light pulse total energy to a desired pre-determined level. As such, this feature will enable a calibrating of the power supplying arrangement or apparatus 12/12a to compensate for a number of phenomenon including the aging of the flash lamp 15 , the 'drifting' of system electronic modules, etc. The optical detection means 90 may be embodied to include one or more available off-the-shelf photo-sensitive devices. One preferred device that may be employed in the detection means 90 is a PIN diode (not illustrated), which would be structured with an optical window to receive and detect the precise sample. Other photo-sensitive devices may be provided by skilled persons.

Returning to FIG. 3, the precise sample of the high energy light pulse that is detected may be converted to an analog signal, or equivalently to a digital value, and delivered to the embedded computer 64 by the feedback signal 88. If it is determined that the level of the feedback signal 88 is too high (indicating the energy level of the light pulse is too high), the operative link 64a may be utilized by the embedded computer 64 to lower a voltage level produced by output 30a that is coupled to the energy storage module 32 from the power supply module 30, thereby reducing the energy collected and stored within module 32. It may be noted that yet another operative link 64b may be provided for adjusting operating parameters of the energy storage module 32, as well as provide information to the embedded computer 64 from the energy storage module.

As would be appreciated by skilled persons, the embedded computer 64 may be provided in many varying forms. For example, standard micro-controller or microprocessor based designs are possible. Alternatively, commercially available single board computers may be employed. In addition, the user interface (not illustrated) may be structured to include a keypad, momentary and maintained switches, annunciators, and possibly a display unit. It is important to understand that any design approach, even possibly those based on custom ASIC devices, that provides the required functionality, as discussed above, is contemplated as being within the scope of the present invention.

Figure 4:
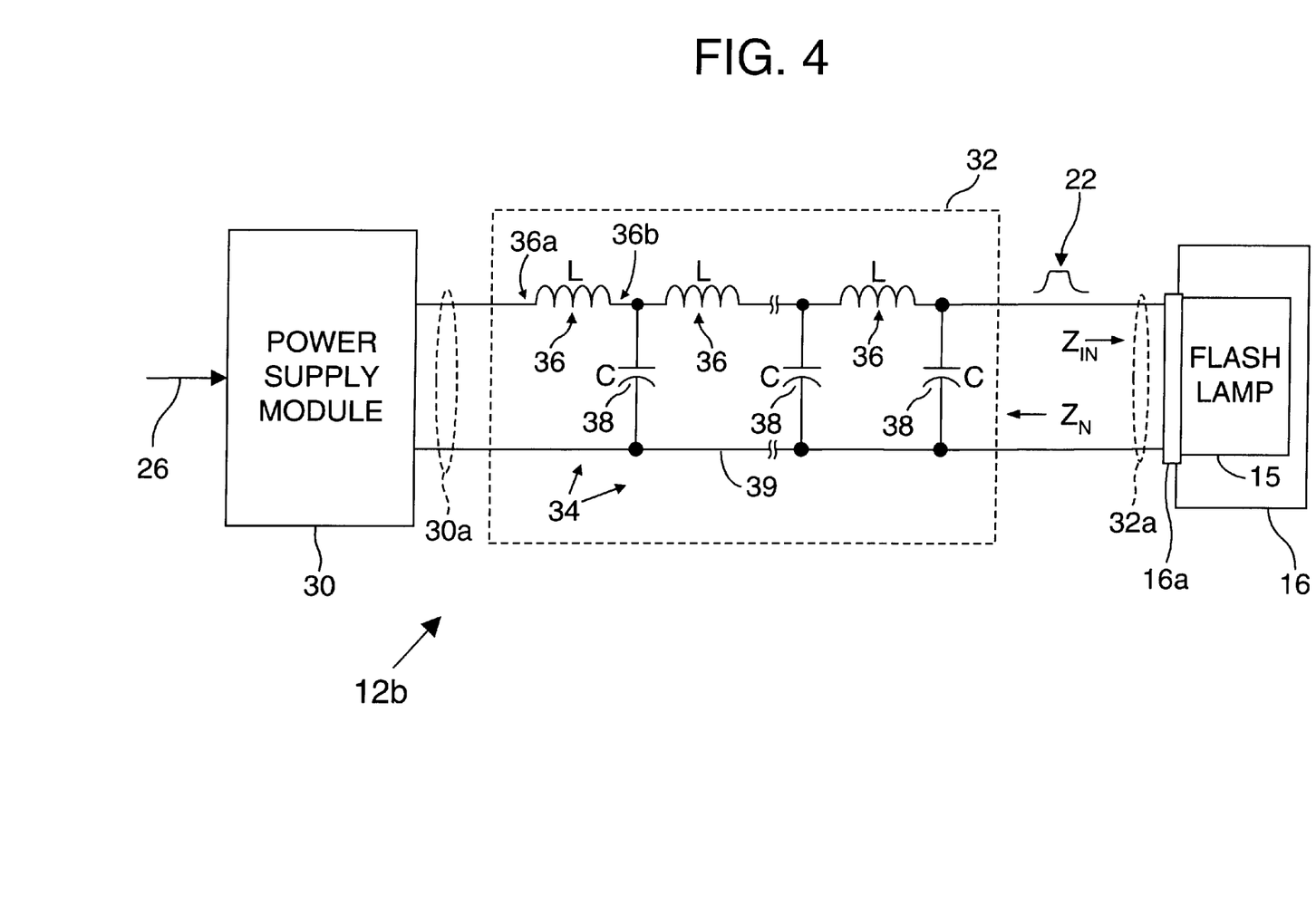
FIG. 4 is a schematic diagram of a possibly most preferred embodiment of an energy storage module, including a 'waveshaping' capability, for producing a flattened and extended current pulse that is coupled and delivered to energize a flash lamp in accordance with the invention.

Turning now to FIG. 4, a possibly most preferred embodiment of an energy supplying arrangement 12b is illustrated. The energy supplying arrangement 12b may be assumed to include the power supply module 30, along with the energy storage module 32. In this preferred embodiment the energy storage module 32 is structured as an essentially passive module. As shown, a charged delay line 34 is structured with lumped capacitive and inductive elements. The charged delay line 34 is employed to provide for energy collecting and storage, along with a waveshaping function to enable the desired amplitude controlled (flattened) and duration controlled (extended) current pulse 22 to be produced and delivered to the flash lamp 15. As discussed above, the current pulse is flattened to limit the peak current to a reduced level. As such, it may be assumed that the delivering of the collected and stored energy in the form of the flattened and extended current pulse, involves producing a current pulse having a peak current at or below a first desired current limit at an upper end of a first linear region of operation. For example, when considering the energizing of a flash lamp that is characterized by the transfer function of FIG. 1A, the desired peak current level of the flattened and extended current pulse would be substantially at or below the relative current level I1 (of FIG. 1A).

As can be seen in FIG. 4, a preferred embodiment of the charged delay line 34 of the energy storage module 32 is structured with a plurality of capacitors 38 and a plurality of inductors 36. As clearly shown, the inductors 36 and capacitors 38 are arranged in what may be termed a 'series-parallel configuration'. Accordingly, the plurality of inductors 36 shown in FIG. 4 are coupled in a cascade or series arrangement, with each inductor 36 having an input terminal 36a and an output terminal 36b. Each respective capacitor 38 is connected between a respective output terminal 36b of each inductor 36 and a common reference (or return) node 39, thus forming the series-parallel configuration. Although the embodiment of the charged delay line 34 is depicted in FIG. 4 as having 3 sections (with each section formed by one inductor 36 and one capacitor 38), any suitable number of sections may be employed, as required to produce a desired flattened and extended current pulse.

An important characteristic of the energy storage module 32 of FIG. 4, is that its impedance $Z_N$, which is determined by the parameter selection and construction of the energy storage module 32, is substantially matched to the impedance of the flash lamp 15 during the interval that the lamp is producing the high energy light pulse. Such a 'matching' of the impedance $Z_N$ to the impedance of the flash lamp, $Z_{IN}$ is critical to achieving optimum energy transfer via the desired amplitude and duration controlled current pulse. The value of $Z_N$ may be assumed to be approximately equal to the square root of the ratio of the inductance L of inductor 36 and the capacitance C of capacitor 38. Therefore, $Z_N$ may be defined by the formula: $Z_N = (L/C)^{1/2}$. Further, the pulse width of the flattened and extended current pulse is approximately equal to 2 times the square root of the product of the total inductance and the total capacitance of the charged delay line 34. Therefore, the length or duration of the pulse width may be calculated by using the formula:

PW Duration=$2 \times [L(total) \times C(total)]^{1/2}$

As will be appreciated by skilled persons, other equivalent arrangements may be provided to embody the energy storage module 32, as well as the charged delay line 34, in accordance with the invention. As such, the embodiment of FIG. 4 is illustrative of a preferred embodiment. Further, it must be noted that more complex, possibly active electronic circuits may be utilized for producing and delivering the flattened (amplitude controlled) and extended (duration controlled) current pulse to the flash lamp 15 in accordance with the invention.

In summary, it is important to understand that a fundamental method of the embodiments of the present invention, including the embodiments of FIG. 2 and FIG. 3, may be described as follows. In order to properly energize a (triggered) flash lamp 15 to produce a high energy light pulse, a first step involves the collecting and storing of energy, say as provided at the output 30a of the power supply module 30. Subsequently, the stored energy is delivered to the flash lamp 15 (of the flash lamp assembly 16) in the form of a flattened and preferably extended current pulse that is coupled to energize the flash lamp. The flattened and extended current pulse is provided by, or coupled from, the output 32a of an energy storage module 32 in order to properly energize the flash lamp 15 to produce the required high energy light pulse. The process may then repeat in a spaced temporal fashion, as required.

While there have been described a plurality of the currently preferred embodiments of the present invention, along with varied methods of operation, those skilled in the art will recognize that other and further modifications may be made without departing from the invention and it is intended to claim all modifications and variations as fall within the scope of the invention and the appended claims.

What is claimed is:

1. A method to energize a triggerable flash lamp to produce a high energy light pulse, the method comprising the steps of:
   (a) collecting and storing energy for delivery to the flash lamp when triggered;
   (b) triggering the flash lamp; and
   (c) delivering the collected and stored energy to the flash lamp in the form of a flattened and extended current pulse coupled to an energy input coupling of the flash lamp, energizing the flash lamp and thereby producing the high energy light pulse.

2. The method as recited in claim 1, wherein the step of collecting and storing energy is supported by an energy storage module that is interposed between an output of a power supply module and the energy input coupling of the flash lamp.

3. The method as recited in claim 1, wherein the step of collecting and storing energy is supported by an energy storage module structured with a charged delay line.

4. The method as recited in claim 3, wherein the step of collecting and storing energy is supported by a charged delay line composed of a series-parallel arrangement of inductors and capacitors providing a simulated lumped-element charged delay line.

5. The method as recited in claim 1, wherein the step of delivering the collected and stored energy in the form of the flattened and extended current pulse, involves a current pulse having a peak current at or below a first desired current limit at an upper end of a first linear region of operation of the flash lamp.

6. A method to energize a triggerable flash lamp structured with an energy input coupling and a trigger input, wherein the triggering of the flash lamp produces a high energy light pulse, the method comprising the steps of:
   (a) collecting and storing energy provided by an output of a DC power supply module; and
   (b) delivering the stored energy to the flash lamp, when triggered, in the form of a flattened and extended current pulse coupled to the energy input coupling of the flash lamp to energize the flash lamp, producing the high energy light pulse.

7. The method as recited in claim 6, wherein the step of delivering the stored energy in the form of a flattened and extended current pulse results in a peak current level of the flattened and extended current pulse being substantially at or below a first desired current limit established substantially at an upper end of a first linear region of operation of the flash lamp.

8. The method as recited in claim 6, wherein the step of collecting and storing energy is supported by interposing a charged delay line between the output of the DC power supply module and the energy input coupling of the flash lamp, with the charged delay line providing for energy storage and waveshaping, enabling the generation and delivery of the flattened and extended current pulse to the flash lamp.

9. The method as recited in claim 8, wherein the delivering of the stored energy to the flash lamp is facilitated by substantially matching an impedance of the charged delay line to an input impedance of the energy input coupling of the flash lamp when producing the high energy light pulse.

10. An energy supplying arrangement for use in energizing a trigger activated flash lamp for periodically producing a high energy light pulse, the energy supplying arrangement comprising:
    (a) a power supply module having an energy providing output; and
    (b) an energy storage module coupled to the energy providing output of the power supply module to collect and store energy supplied thereby, the energy storage module having an output that is coupled to the flash lamp, the output of the energy storage module configured with a characteristic output impedance substantially matched to an input impedance of the flash lamp during an interval when the flash lamp is producing the high energy light pulse;
    (c) the energy storage module structured to deliver a flattened and extended current pulse that is coupled from the output of the energy storage module to an energy input coupling of the flash lamp for energizing the flash lamp, producing the high energy light pulse.

11. The energy supplying arrangement according to claim 10, wherein the energy storage module includes a charged delay line which provides energy storage and waveshaping functions for producing the flattened and extended current pulse when the flash lamp is triggered.

12. The energy supplying arrangement according to claim 11, wherein the charged delay line includes a plurality of cascaded discrete inductors and a plurality of discrete capacitors connected between at an output terminal of each respective inductor and a common reference node.

13. The energy supplying arrangement according to claim 11, wherein the charged delay line includes a plurality of inductors and a plurality of capacitors coupled in a serial-parallel configuration.

* * * * *

(12) EX PARTE REEXAMINATION CERTIFICATE (7027th)
United States Patent
Bertan et al.

(10) Number: US 6,719,753 C1
(45) Certificate Issued: Aug. 25, 2009

(54) MEANS AND METHOD FOR ENERGIZING A FLASH LAMP

(76) Inventors: Howard Stephen Bertan, 41 Moss La., Jericho, NY (US) 11753; Kenneth Lawrence Short, 142 Quaker Path, Setauket, NY (US) 11733

Reexamination Request:
No. 90/010,269, Sep. 4, 2008

Reexamination Certificate for:
Patent No.: 6,719,753
Issued: Apr. 13, 2004
Appl. No.: 10/177,971
Filed: Jun. 22, 2002

Related U.S. Application Data

(62) Division of application No. 09/384,122, filed on Aug. 27, 1999, now Pat. No. 6,461,348.

(51) Int. Cl.
*A61B 18/18* (2006.01)

(52) U.S. Cl. .................. 606/9; 315/200 A; 315/214; 315/241 R; 315/244

(58) Field of Classification Search ................ None
See application file for complete search history.

(56) References Cited
PUBLICATIONS

Goldman, Leon and R. James Rockwell, Jr., "Lasers in Medicine," Gordon and Breach, Science Publishers, Inc., 1971, pp. 44–52.*

* cited by examiner

*Primary Examiner*—Jeanne M Clark (57) ABSTRACT

A method and structure for energizing a flash lamp for producing a high energy light pulse, with the flash lamp energized by a flattened and extended current pulse. The method includes collecting and storing energy for delivery to the flash lamp when trigerred. A triggering of the flash lamp resulting in a delivering of the collected and stored energy to the flash lamp in the form of an amplitude controlled (flattened) and duration controlled (extended) current pulse.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–13 are cancelled.

\* \* \* \* \*